(12) United States Patent
Nyhus

(10) Patent No.: US 7,294,773 B1
(45) Date of Patent: Nov. 13, 2007

(54) HYBRID CORN LINE G4901

(75) Inventor: Kris Nyhus, New Ulm, MN (US)

(73) Assignee: Syngenta (AT) Limited, Surrey (GB)

( * ) Notice: Subject to any disclaimer, the term of this patent is extended or adjusted under 35 U.S.C. 154(b) by 284 days.

(21) Appl. No.: 10/931,941

(22) Filed: Sep. 1, 2004

Related U.S. Application Data

(63) Continuation of application No. 09/811,049, filed on Mar. 15, 2001, now Pat. No. 6,828,492.

(51) Int. Cl.
| | |
|---|---|
| A01H 5/10 | (2006.01) |
| A01H 5/00 | (2006.01) |
| A01H 1/00 | (2006.01) |
| C12N 15/82 | (2006.01) |
| C12N 5/04 | (2006.01) |

(52) U.S. Cl. .................. 800/320.1; 435/468; 800/275; 800/298; 800/300.1; 800/302

(58) Field of Classification Search ................... None
See application file for complete search history.

(56) References Cited

U.S. PATENT DOCUMENTS

| | | | |
|---|---|---|---|
| 5,177,010 A | | 1/1993 | Goldman et al. |
| 5,302,523 A | | 4/1994 | Coffee et al. |
| 5,464,765 A | | 11/1995 | Coffee et al. |
| 5,484,956 A | | 1/1996 | Lundquist et al. |
| 5,489,520 A | | 2/1996 | Adams et al. |
| 5,596,838 A | | 1/1997 | Greaves et al. |
| 5,763,753 A | * | 6/1998 | Maves .................. 800/320.1 |

FOREIGN PATENT DOCUMENTS

EP   0 160 390   3/1985

OTHER PUBLICATIONS

Conger, B.V., F.J. Novak, R. Afza, and K. Erdelsky. "Somatic embryogenesis from cultured leaf segments of *Zea mays*", Plant Cell Reports, 6:345-347 (1987).

Duncan, D.R., M.E. Williams, B.E. Zehr and J.M. Widholm. "The production of callus capable of plant regeneration from immature embryos of numerous *Zea mays* genotypes", Planta, 165:322-332 (1985).

Edallo, et al., "Chromosomal Variation and Frequency of Spontaneous Mutation Associated with in Vitro Culture and Plant Regeneration in Maize" Maydica XXVI, pp. 39-56 (1981).

Forsberg, R.A. and R.R. Smith. "Sources, Maintenance, and Utilization of Parental Material", Hybridization of Crop Plants, Chapter 4, pp. 65-81 (1980).

Green, C.E. and R.L. Phillips. "Plant Regeneration from Tissue Cultures of Maize", Crop Science, vol. 15, pp. 417-421 (1975).

Green, C.E. and C.A. Rhodes. "Plant Regeneration in Tissue Cultures of Maize", Maize for Biological Research, pp. 367-372 (1982).

Hallauer, et al, "Corn Breeding", Corn and Corn Improvement pp. 463-564 (1988). Sprague et al, eds.

Meghji, M.R., J.W. Dudley, R.J. Lambert, and G.F. Sprague. "Inbreeding Depression, Inbred and Hybrid Grain Yields, and Other Traits of Maize Genotypes Representing Three Eras". Crop Science, vol. 24, pp. 545-549 (1984).

Poehlman, John Milton. Breeding Field Crop, AVI Publishing Company, Inc., Westport, Connecticut, pp. 237-246 (1987).

Tomes, et al, "The Effect of Parental Genotype on Initiation of Embryogenic Callus from Elite Maize (*Zea mays* I.) Germplasm". Theor. Appl. Genet. 70., pp. 505-509. (1985).

Troyer, et al., "Selection for Early Flowering in Corn: 10 Late Synthetics". Crop Science, vol. 25, pp. 695-697 (1985).

Umbeck, et al. "Reversion of Male-Sterile T-Cytoplasm Maize to Male Fertility in Tissue Culture", Crop Science vol. 23, pp. 584-588 (1983).

Wright, H., "Commerical Hybrid Seed Production", Hybridization of Crop Plants, pp. 161-176, (1980).

Wych, R.D., "Production of Hybrid Seed Corn"; Corn and Corn Improvement, pp. 565-607 (1988).

* cited by examiner

*Primary Examiner*—Ashwin Mehta
(74) *Attorney, Agent, or Firm*—Dana Rewoldt

(57) ABSTRACT

Broadly this invention provides an inbred corn line G4901. The methods for producing a corn plant by crossing the inbred line G4901 are also encompassed by the invention. Additionally, the invention relates to the various parts of inbred G4901 including culturable cells. This invention relates to hybrid corn seeds and plants produced by crossing the inbred line G4901 with at least one other corn line.

16 Claims, No Drawings

HYBRID CORN LINE G4901

This is a continuation of prior application Ser. No. 09/811,049, filed Mar. 15, 2001, and issued as U.S. Pat. No. 6,828,492.

FIELD OF THE INVENTION

This invention is in the field of corn breeding, specifically relating to an inbred corn line designated G4901. This invention also is in the field of hybrid maize production employing the present inbred.

BACKGROUND OF THE INVENTION

The original maize plant was indigenous to the Western Hemisphere. The plants were weedlike and only through the efforts of early breeders were cultivated crop species developed. The crop cultivated by early breeders, like the crop today, could be wind pollinated. The physical traits of maize are such that wind pollination results in self-pollination or cross-pollination between plants. Each plant has a separate male and female flower that contributes to pollination, the tassel and ear, respectively. Natural pollination occurs when wind transfers pollen from tassel to the silks on the corn ears. This type of pollination has contributed to the wide variation of maize varieties present in the Western Hemisphere.

Originally, when maize was an open pollinated variety having heterogeneous genotypes, the maize farmer selected uniform ears from the yield of these genotypes and preserved them for planting the next season. The result was a field of maize plants that segregated for a variety of traits. This type of maize selection led to, at most, incremental increases in seed yield.

The development of a planned breeding program for maize occurred in the early 1920's or thereabout. A large part of the development of planned breeding program for transforming the maize product into a profitable agricultural crop was due to the work done by land grant colleges in the Midwest of the United States. Large increases in seed yield were due to the development of numerous hybrid corn varieties from these planned breeding programs.

Hybrids were developed by selecting corn lines and selfing these lines for several generations to develop homozygous pure inbred lines. One selected inbred line was crossed with another selected inbred line to produce hybrid progeny (F1). Although hybrids, due to heterosis, are robust and vigorous plants, inbreds on the other hand are mostly homozygous. This homozygosity renders the inbred lines less vigorous. Inbred seed can be difficult to produce since the inbreeding process in corn lines decreases the vigor. However, when two inbred lines are crossed, the hybrid plant evidences greatly increased vigor and seed yield compared to open pollinated, segregating maize plants. An important consequence of the homozygosity and the homogeneity of the inbred maize lines is that all hybrid seed produced from any cross of two such elite lines will be the same hybrid seed and make the same hybrid plant. Thus the use of two inbreds (one acting as the female and one acting as the male) makes hybrid seed which can be reproduced readily. The hybrid plant in contrast does not produce hybrid seed that is readily reproducible. The seed on a hybrid plant is F2 and segregating for traits.

The ultimate objective of the commercial maize seed companies is to produce high yielding, agronomically sound plants that perform well in certain regions or areas of the Corn Belt. To produce these types of hybrids, the companies must develop inbreds, which carry needed traits into the hybrid combination. Hybrids are not often uniformly adapted for the entire Corn Belt, but most often are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois and Iowa soil. Thus, a variety of major agronomic traits are important in hybrid combination for the various Corn Belt regions, and have an impact on hybrid performance.

Inbred line development and hybrid testing have been emphasized in the past half-century in commercial maize production as a means to increase hybrid performance. Inbred development is usually done by pedigree selection. Pedigree selection can be selection in a $F_2$ population produced from a planned cross of two genotypes (often elite inbred lines), or a selection of progeny of synthetic varieties, open pollinated, composite, or backcrossed populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include: yield potential in hybrid combination; dry down; maturity; grain moisture at harvest; greensnap; resistance to root lodging; resistance to stalk lodging; grain quality; disease and insect resistance; ear and plant height. Additionally, hybrid performance will differ in different soil types such as low levels of organic matter, clay, sand, black, high pH, low pH; or in different environments such as wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are regrettably not single dominant genes but are multi-genetic with additive gene action not dominant gene action. Thus, the general procedure of producing a non segregating $F_1$ generation and self pollinating to produce a $F_2$ generation that segregates for traits and selecting progeny with the visual traits desired does not easily lead to a useful inbred. Great care and breeder expertise must be used in selection of breeding material to continue to increase yield and the agronomics of inbreds and resultant commercial hybrids.

Certain regions of the Corn Belt have specific difficulties that other regions may not have. Thus the hybrids developed from the inbreds have to have traits that overcome or at least minimize these regional growing problems. Examples of these problems include in the eastern corn belt Gray Leaf Spot, in the north cool temperatures during seedling emergence, in the Nebraska region CLN (corn Lethal necrosis and in the west soil that has excessively high pH levels. The industry often targets inbreds that address these issues specifically forming niche products. However, the aim of most large seed producers is to provide a number of traits to each inbred so that the corresponding hybrid can useful in a broader regions of the Corn Belt. The new biotechnology techniques such as Microsatellites, RFLPs, RAPDs and the like have provided breeders with additional tools to accomplish these goals.

SUMMARY OF THE INVENTION

The present invention relates to an inbred corn line G4901. Specifically, this invention relates to plants and seeds of this inbred line. Additionally, this invention relates to a method of producing from this inbred, hybrid seed corn and hybrid plants with seeds from such hybrid seed. More particularly, this invention relates to the unique combination of traits that combine in corn line G4901.

Generally then, the present invention includes an inbred corn seed designated G4901. This seed produces a corn plant.

The invention also includes the tissue culture of regenerable cells of G4901 wherein the cells of the tissue culture regenerates plants capable of expressing the genotype of G4901. The tissue culture is selected from the group consisting of: leaves, pollen, embryos, roots, root tips, guard cells, ovule, seeds, anthers, silk, flowers, kernels, ears, cobs, husks and stalks, cells and protoplasts thereof. The corn plant regenerated from G4901 or any part thereof is included in the present invention. The present invention includes regenerated corn plants that are capable of expressing G4901's genotype, phenotype or mutants or variants thereof.

The invention extends to hybrid seed produced by planting, usually in pollinating proximity (this invention includes using preserved maize pollen as explained in U.S. Pat. No. 5,596,838 to Greaves), seeds of corn inbred lines G4901 and another inbred line if preserved pollen is not used; cultivating corn plants resulting from said planting; preventing pollen production by the plants of one of the inbred lines if two are employed; allowing cross pollination to occur between said inbred lines; and harvesting seeds produced on plants of the selected inbred. The hybrid seed produced by hybrid combination of plants of inbred corn seed designated G4901 and plants of another inbred line are apart of the present invention. This inventions scope covers hybrid plants and the plant parts including the grain and pollen grown from this hybrid seed.

The invention further includes a method of hybrid F1 production. A first generation (F1) hybrid corn plant produced by the process of planting seeds of corn inbred line G4901; cultivating corn plants resulting from said planting; permitting pollen from another inbred line to cross pollinate inbred line G4901; harvesting seeds produced on plants of the inbred; and growing a harvested seed are part of the method of this invention.

Likewise included in this invention, is a first generation (F1) hybrid corn plant produced by the process of planting seeds of corn inbred line G4901; cultivating corn plants resulting from said planting; permitting pollen from inbred line G4901 to cross pollinate another inbred line; or in the alternative permitting pollen from another inbred line to pollinate the inbred line G4901, harvesting seeds produced on plants of the inbred; and growing a plant from such a harvested seed.

The inbred corn line G4901 and at least one transgenic gene adapted to give G4901 additional and/or altered traits are within the scope of the invention. Such transgenes are usually present in the corn line in association with regulatory elements (promoters, enhancers, terminators and the like). Presently, trangenes provide the invention with traits such as insect resistance, herbicide resistance, disease resistance, increased or deceased or altered starches, sugars or oils, increased or decreased life cycle or other altered trait.

The present invention includes inbred corn line G4901 and at least one transgenic gene adapted to give G4901 modified starch traits. Furthermore this invention includes the inbred corn line G4901 and at least one mutant gene adapted to give modified starch, acid or oil or herbicide resistance traits. The present invention includes the inbred corn line G4901 and at least one transgenic gene selected from the group consisting of: *bacillus thuringiensis*, the bar or pat gene encoding phosphinothricin acetyl transferase, Gdha gene, EPSP synthase gene, low phytic acid producing gene, and zein. The inbred corn line G4901 and at least one transgenic gene useful as a selectable marker or a screenable marker are covered by the present invention.

A tissue culture of the regenerable cells of hybrid plants produced with use of G4901 genetic material is covered by this invention. A tissue culture of the regenerable cells of the corn plant produced by the method described above are also included.

DEFINITIONS

In the description and examples, which follow, a number of terms are used. In order to provide a clear and consistent understanding of the specifications and claims, including the scope to be given such terms, the following definitions are provided.

BL MOIST

The moisture percentage of the grain at black layer, i.e., when 50% of the plants per plot have reached physiological maturity.

COLD GERM

Cold Germ is a measurement of seed germination under cold soil conditions. Data is reported as percent of seed germinating.

ECB

European corn borer is a maize eating insect. ECBI is the first brood generation of European corn borers. ECBII is the second generation of European corn borers.

EMERGE (EMG)

The number of emerged plants per plot (planted at the same seedling rate) collected when plants have two fully developed leaves.

GI

This is a selection index that provides a single quantitative measure of the worth of a hybrid based on four traits. FI is a very similar index which weights yield less than GI. In GI yield is the primary trait contributing to index values. The GI value is calculated by combining stalk lodging, root lodging, yield and dropped ears according to the attached mathematical formula:

$$GI=100+0.5(YLD)-0.9(\% \text{ STALK LODGE})-0.9(\% \text{ ROOT LODGE})-2.7(\% \text{ DROPPED EAR})$$

GLS

Gray Leaf Spot (*Cercospora Zeae*) disease rating. This is rated on a 1-9 scale with a "1" being very susceptible, and a "9" being very resistant.*

GW

Goss' Wilt (*Corynebacterium nebraskense*). This is rated on a 1-9 scale with a "1" being very susceptible, and a "9" being very resistant.*

HEATP10

The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \frac{(\text{Max Temp } (°F) + \text{Min Temp } (°F))}{2} - 50$$

The highest maximum temperature used is 86° F. and the lowest minimum temperature used is 50° F. For each inbred or hybrid it takes a certain number of GDU's to reach various stages of plant development.

HEATBL

The number of GDU's after planting when approximately 50 percent of the inbred or hybrid plants in a plot have grain that has reached physiological maturity (black layer).

HEATPEEK

The number of GDU's after planting of an inbred when approximately 50 percent of the plants show visible tassel extension.

HEATP50 or HTP50

The number of GDU's required for an inbred or hybrid to have approximately 50 percent of the plants shedding pollen. Growing Degree Units are calculated by the Barger Method as shown in the HEATP10 definition.

HEATP90

The number of GDU's accumulated from planting when the last 100 percent of plants in an inbred or hybrid are still shedding enough viable pollen for pollination to occur. Growing Degree Units are calculated by the Barger Method as shown in the HEATP10 definition.

HEATS10

The number of GDU's required for an inbred or hybrid to have approximately 10 percent of the plants with silk emergence of at least 0.5 inches. Growing Degree Units are calculated by the Barger Method as shown in the HEATP10 definition.

HEATS50 or HTS50

The number of GDU's required for an inbred or hybrid to have approximately 50 percent of the plants with silk emergence of at least 0.5 inches. Growing Degree Units are calculated by the Barger Method as shown in the HEATP10 definition.

HEATS90

The number of GDU's required for an inbred or hybrid to have approximately 90 percent of the plants with silk emergence of at least 0.5 inches. Growing Degree Units are calculated by the Barger Method as shown in the HEATP10 definition.

$MDMV_A$

Maize Dwarf Mosaic Virus strain A. The corn is rated on a 1-9 scale with a "1" being very susceptible, and a "9" being very resistant.*

$MDMV_B$

Maize Dwarf Mosaic Virus strain B. This is rated on a 1-9 scale with a "1" being very susceptible and a "9" being very resistant.*

MOISTURE

The average percentage grain moisture of an inbred or hybrid at harvest time.

NLB

Northern Leaf Blight (*Exserohilum turcicum*) disease rating. This is rated on a 1-9 scale with a "1" being very susceptible, and a "9" being very resistant.*

PCT TILLER

The total number of tillers per plot divided by the total number of plants per plot.

PLANT

This term includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like, and this term also includes any transgenic DNA or (RNA) or portion thereof that have been introduced into the plant by whatever method.

PLANT HEIGHT (PLTHT) (PHT)

The distance in centimeters from ground level to the base of the tassel peduncle.

PLANT INTEGRITY (PLTINT) or (INT)

The level of plant integrity on a scale of 1-9 with 9 evidencing the trait most strongly: 1-2.9 ratings are low plant integrity, 3-5.9 ratings are intermediate plant integrity, and 6-9 ratings are strongly evidencing plant integrity.

POPULATION (POP)

The plant population.

RM

Predicted relative maturity based on the moisture percentage of the grain at harvest. This rating is based on known set of checks and utilizes standard linear regression analyses and is referred to as the Minnesota Relative Maturity Rating System.

SHED

The volume of pollen shed by the male flower rated on a 1-9 scale where a "1" is a very light pollen shedder, a "4.5" is a moderate shedder, and a "9" is a very heavy shedder.

SLB

Southern Leaf Blight (*Bipolaris maydis*) disease rating. This is rated on a 1-9 scale with a "1" being very susceptible, and a "9" being very resistant.*

STAYGREEN (SGN)

The level of staygreen of the plant on a scale of 1-9 with 9 evidencing the trait most strongly: 1-2.9 ratings are low staygreen, 3-5.9 ratings are intermediate staygreen, and 6-9 ratings are strongly evidencing staygreen.

TWT

The measure of the weight of grain in pounds for a one bushel volume adjusted for percent grain moisture.

VIGOR (VIG)

Visual rating of 1 to 9 made 2-3 weeks post-emergence where a "1" indicates very poor early plant development, and a "9" indicates superior plant development.

WARM GERM

A measurement of seed germination under ideal (warm, moist) conditions. Data is reported as percent of seeds germinating.

YIELD (YLD)

Actual yield of grain at harvest adjusted to 15.5% moisture. Measurements are reported in bushels per acre.

% DROPPED EARS (DE)

The number of plants per plot, which dropped their primary ear, divided by the total number of plants per plot.

% LRG FLAT

Percentage by weight of shelled corn that passes through a 26/64 inch round screen and a 14/64 inch slot screen, but does not pass through a screen with 20.5/64 inch round openings.

% LRG ROUND

Percentage by weight of shelled corn that passes through a 26/64 inch round screen, but does not pass through a 14/64 inch slot screen or a screen with 20.5/64 inch round openings.

% MED FLAT

Percentage by weight of shelled corn that passes through a 20.5/64 inch round screen and a 13/64 inch slotted screen, but does not pass through a screen with 17/64 inch round openings.

% MED ROUND

Percentage by weight of shelled corn that passes through a 20.5/64 inch round screen, but does not pass through a 13/64 inch slot screen or a screen with 17/64 inch round openings.

% SML FLAT

Percentage by weight of shelled corn that passes through a 17/64 inch round screen and a 12/64 inch slotted screen, but does not pass through a screen with 15/64 inch round openings.

% SML ROUND

Percentage by weight of shelled corn that passes through a 17/64 inch round screen, but does not pass through a 12/64 inch slotted screen or a screen with 15/64 inch round openings.

% ROOT LODGE (RL)

Percentage of plants per plot leaning more that 30 degrees from vertical divided by total plants per plot.

% STALK LODGE (SL)

Percentage of plants per plot with the stalk broken below the primary ear node divided by the total plants per plot.

*Resistant—on a scale of 1-9 with 9 evidencing the trait most strongly: 1-2.9 ratings are susceptible, 3-5.9 ratings are intermediate, and 6-9 ratings are resistant.

DETAILED DESCRIPTION OF THE INVENTION

G4901 can be used as a female line. This inbred is useful as a female because it has nice seed producing traits, including excellent germination traits. In hybrid combination this line yields hybrids with good test weights and excellent yield potential. The inbred carries a average levels of tolerance to Eye Spot. When used as a male the G4901 line shows a disadvantage in having an lower than average shed.

The inbred has shown uniformity and stability within the limits of environmental influence for all the traits as described in the Variety Description Information (Table 1) that follows.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in G4901.

The best method of producing the invention, G4901 which is substantially homozygous, is by planting the seed of G4901 which is substantially homozygous and self-pollinating or sib pollinating the resultant plant in an isolated environment, and harvesting the resultant seed.

TABLE 1

| | G4901 VARIETY DESCRIPTION INFORMATION | |
|---|---|---|
| #1 | Type: Dent | |
| #2 | Region Best Adapted: In the region adapted for RM of 111. | |
| #3 | Plant Traits | |
| | Plant Height | 68 in. |
| | Ear Height | 31 in. |
| | Tillers (Rating) | 5 |
| | Leaf Color | LIGHT GREEN |
| | Brace Root Color | GREEN |
| | Silk Color | YELLOW |
| | Shoots at Flowering | BALD |
| #4 | Tassel Traits | |
| | Glume Color | GREEN/PURPLE |
| | Glume Ring Color | YELLOW |
| | Anther Color | PURPLE |
| #5 | Ear and Kernel Traits | |
| | Cob Color | WHITE |
| | Kernel Crown Color | BRIGHT YELLOW |
| | Kernel Body Color | DARK YELLOW |
| #6 | DISEASE RESISTANCE IN INBRED G4901 | |
| | Eye Spot = 5.1 | |
| | Gross wilt = 4 | |
| | Northern leaf blight = 1.0 | |
| #7 | INSECT RESISTANCE IN INBRED | |
| | ECB1 = 6.75 | |
| | ECB2 = 4.76119 | |
| | Ear rate = 3.50000 | |
| #8 | The comparable inbred to G4901 is ZS01595, an inbred having a number of similarities. ZS01595 is an inbred which has been or is presently in a number of commercial hybrids that are in a similar region of adaption as most of the hybrids formed with G4901. | |

The Munsell code is a reference book of color, which is known and used in the industry and by persons with ordinary skill in the art of plant breeding.

The purity and homozygosity of inbred G4901 is constantly being tracked using isozyme genotypes as shown in Table 2.

Isozyme Genotypes for G4901

Isozyme data were generated for inbred corn line G4901 according to procedures known and published in the art. The data in Table 2 gives the electrophoresis data on G4901 as compared to its two parents.

TABLE 2

ELECTROPHORESIS RESULTS FOR G4901

| INBRED | ACP1 | ACP4 | ADH | MDH1 | MDH2 | PGD1 | PGD2 | PHI | PGM | IDH |
|---|---|---|---|---|---|---|---|---|---|---|
| G4901 | 11 | 00 | 22 | 22 | 11 | 11 | 11 | 22 | 22 | 22 |

Inbred and Hybrid Performance of G4901

The traits and characteristics of inbred corn line G4901 are listed to compare with other inbreds and/or in hybrid combination. The G4901 data shows the characteristics and traits of importance, giving a snapshot of G4901 in these specific environments.

Table 3A shows a comparison between G4901 and a comparable inbred ZS01595. G4901 and inbred ZS01595 have similar seedling emergence ratings. G4901 has significantly higher yield at harvest than does ZS01595 in this environment but G4901 also has significantly higher moisture. The present invention reaches heat peak at slightly more heat units than ZS01595.

TABLE 3A

G4901

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVERALL | G4901 |  | 83.5 |  | 161.0 | 74.8 |  | 3.5 |  |
|  | ZS01595 |  | 84.7 |  | 187.6 | 89.2 |  | 4.0 |  |
|  | # EXPTS |  | 4 |  | 4 | 4 |  | 4 |  |
|  | DIFF |  | 1.2 |  | 26.7 | 14.4 |  | 0.5 |  |
|  | PROB |  | 0.676 |  | 0.027** | 0.019** |  | 0.391 |  |

| YEAR | INBRED | HEATP10 | HEATP50 | HEATP90 | HEATS10 | HEATS50 | HEATS90 |
|---|---|---|---|---|---|---|---|
| OVERALL | G4901 | 1377 | 1411 | 1539 | 1374 | 1403 | 1446 |
|  | ZS01595 | 1389 | 1415 | 1565 | 1417 | 1456 | 1498 |
|  | # EXPTS | 4 | 4 | 4 | 4 | 4 | 4 |
|  | DIFF | 12 | 5 | 26 | 44 | 53 | 52 |
|  | PROB | .450 | 0.611 | 0.216 | 0.157 | 0.096* | 0.117 |

| YEAR | INBRED | HEATPEAK | HEATBL | BL MOIST | % ROOT LODGE | % STALK LODGE | % DROP EARS | MOISTURE | YIELD |
|---|---|---|---|---|---|---|---|---|---|
| OVERALL | G4901 | 1347 |  |  |  |  |  | 13.6 | 83.4 |
|  | ZS01595 | 1314 |  |  |  |  |  | 9.9 | 43.9 |
|  | # EXPTS | 4 |  |  |  |  |  | 4 | 4 |
|  | DIFF | 33 |  |  |  |  |  | 3.7 | 39.5 |
|  | PROB | 0.161 |  |  |  |  |  | 0.023** | 0.007*** |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVERALL | G4901 | 95.5 | 91.8 |  |  |  |  |  |  |
|  | ZS01595 | 93.7 | 85.3 |  |  |  |  |  |  |
|  | # EXPTS | 4 | 4 |  |  |  |  |  |  |
|  | DIFF | 1.8 | 6.5 |  |  |  |  |  |  |
|  | PROB | 0.240 | 0.141 |  |  |  |  |  |  |

*.05 < PROB <= .10
**.01 < PROB <= .05
***.00 < PROB <= .01

TABLE 3B

G4901

| YEAR | HYBRID | % ROOT LODGE | % STALK LODGE | % DROP EARS | TEST WEIGHT | MOISTURE | YIELD | GI |
|---|---|---|---|---|---|---|---|---|
| OVERALL | ItG4901 Hybrid | 2.9 | 9.2 | 0.0 | 56.2 | 21.0 | 165.0 | 171.6 |
|  | Cl Hybrid | 0.9 | 5.1 | 0.0 | 55.8 | 18.5 | 159.0 | 174.1 |
|  | # EXPTS | 101 | 101 | 101 | 99 | 101 | 101 | 101 |
|  | DIFF | 2.0 | 4.2 | 0.0 | 0.3 | 2.5 | 6.0 | 2.5 |
|  | PROB | 0.063* | 0.000*** | 0.320 | 0.015** | 0.000*** | 0.004*** | 0.115 |

TABLE 3B-continued

| | | G4901 | | |
|---|---|---|---|---|
| YEAR | HYBRID | MATURITY | V M | Fl |
| OVERALL | ItG4901 Hybrid | | 8.2 | 123 |
| | Cl Hybrid | | 8.9 | 132 |
| | # EXPTS | | 101 | 101 |
| | DIFF | | 0.7 | 8.2 |
| | PROB | | 0.000*** | 0.000*** |

*.05 < PROB <= .10
**.01 < PROB <= .05
***.00 < PROB <= .01

Table 3 b shows the inbred G4901 in hybrid combination with a common inbred and compares this G4901 hybrid with another hybrid combination that includes the same common inbred and yet another inbred. Both of the common inbreds differ slightly in that one carries the IT (imazethapyr tolerance trait) and the other common inbred does not carry this gene mutation. When in these hybrid combinations, the present inbred carries slightly more heavier test weight and a distinctively significant increase in yield levels into the hybrid. The Y/M for the hybrid combination containing the present invention is significantly lower than is the comparison hybrids.

Table 4 shows the GCA (general combining ability) estimates of G4901 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data are from other companies' hybrids, particularly the leaders in the industry in the area of adaption and Garst Seed Company's commercial products, which were grown in the same sets and locations.

TABLE 4

| | N | FI | Y/M | GI | YLD | MST | % SL | % RL | % DE | TWT | POP | RM |
|---|---|---|---|---|---|---|---|---|---|---|---|---|
| | | | | | G4901 | | | | | | | |
| XT = | 26 | −5.1 | −0.7 | −2.6 | −2.0 | −1.1 | −0.7 | −1.2 | 0.0 | 0.4 | −125 | 111 |
| | | | | | ZS01595 | | | | | | | |
| XT = | 1 | −15.7 | −1.0 | −15.9 | −17.2 | 0.1 | −8.4 | 0.1 | 0.0 | 1.3 | 118 | 109 |

$FI = 100 + 0.5(Yld) - 2.3(MST) - 0.9(\% SL) - 0.9(\% RL) - 2.7(\% DE)$

POP=plants per acre

RM=The Minnesota Relative Maturity

XT=GCA Estimate weighted by parent 2, but using only those parent 2 with two years of data Table 4 shows G4901 in XT crossed to different inbreds to form 26 hybrid combinations. G4901 in hybrid combination shows an much less disadvantage for yield compared to the other inbred when in hybrid combination. The yield is different between the two as is the test weight carried into the combinations.

TABLE 5A

| | YIELD RESPONSE Research Plots | | | | | |
|---|---|---|---|---|---|---|
| HYBRID | | | YIELD | | | |
| G4901/Inbred X | 80 | 104 | 129 | 153 | 177 | 201 |
| Environment | 75 | 100 | 125 | 150 | 175 | 200 |

Error: 13.4
Plots 237

TABLE 5B

| | YIELD RESPONSE Research Plots | | | | | |
|---|---|---|---|---|---|---|
| HYBRID | | | YIELD | | | |
| Commercial hybrid | 71 | 96 | 120 | 145 | 169 | 194 |
| Environment | 75 | 100 | 125 | 150 | 175 | 200 |

Error: 14.1
Plots 2700

Table 5A shows the yield response of G4901 in hybrid combination in comparison with the plants in the environment around it at the same location. The data for the present inbred is showing consistently better results than the data of the comparison hybrid through each level of environment. G4901 in hybrid combination, is a workhorse inbred that works well by providing yields better than the environment in low, medium and high yielding environments. Its performance shows that this is a consistent yielding inbred regardless of the environment. Table 5b shows the data from a different hybrid that was formed with the same inbred X. This comparison hybrid is still yielding slightly below the environments and it is not carrying the yield potential into the hybrid as well as the hybrid combination of the present invention. The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line G4901. Further, both first and second parent corn plants can come from the inbred corn line G4901. A variety of breeding methods can be selected depending on the mode of reproduction, the trait, the condition of the germplasm. Thus, any such methods using the inbred corn line G4901 are part of this invention: selfing, backcrosses, hybrid production, crosses to populations, haploid by such old and known methods of using stock material that induces haploids and anther culturing and the like. Additionally, this maize can, within the scope of the invention, contain: a mutant gene such as but not limited to sugary 1 or shrunken 1 or waxy or AE or imazethapyr tolerant (IT or IR™) mutant gene; or transgenic genes such as but not limited to insect resistant genes such as *Bacillus thuringiensis* (Cry genes), or herbicide resistant genes such as Pat gene or Bar gene, EPSP, or disease resistant genes such as the Mosaic virus resistant gene, etc., or trait altering genes such as flowering genes, oil modifying genes, senescence genes and the like.

Various culturing techniques known to those skilled in the art, such as haploid, (stock six is a method that has been in use for twenty years and is well known to those with skill in the art), transformation, and a host of other conventional and unconventional methods are within the scope of the invention. All plants and plant cells produced using the inbred corn line are within the scope of this invention. The term transgenic plant refers to plants having genetic sequences, which are introduced into the genome of a plant by a transformation method and the progeny thereof.

Transformation Methods—are means for integrating new genetic coding sequences into the plant's genome by the incorporation of these sequences into a plant through man's assistance.

There are a large number of known methods to transform plants. The basic steps of transforming plants including monocots and dicots are known in the art. The example of these steps are concisely outlined in U.S. Pat. No. 5,484,956 "Fertile Transgenic *Zea mays* Plants Comprising Heterologous DNA Encoding *Bacillus Thuringiensis* Endotoxin" issued Jan. 16, 1996 and U.S. Pat. No. 5,489,520 "Process of Producing Fertile *Zea mays* Plants and Progeny Comprising a Gene Encoding Phosphinothricin Acetyl Transferase" issued Feb. 6, 1996.

Plant cells such as maize can be transformed by a number of different techniques. Some of these techniques which have been reported on and are known in the art include maize pollen transformation (See University of Toledo 1993 U.S. Pat. No. 5,177,010); biolistic gun technology (See U.S. Pat. No. 5,484,956); whiskers technology (See U.S. Pat. Nos. 5,464,765 and 5,302,523); electroporation; PEG on Maize; *Agrobacterium* (See 1996 article on transformation of maize cells in *Nature Biotechnology, Volume* 14, June 1996) along with numerous other methods which may have slightly lower efficiency rates then those listed. Some of these methods require specific types of cells and other methods can be practiced on any number of cell types.

The use of pollen, cotyledons, meristems and ovum as the target issue can eliminate the need for extensive tissue culture work. However, the present state of the technology does not provide very efficient use of this material.

Generally, cells derived from meristematic tissue are useful. Zygotic embryos can also be used. Additionally, the method of transformation of meristematic cells of cereal is also taught in the PCT application WO96/04392. Any of the various cell lines, tissues, plants and plant parts can and have been transformed by those having knowledge in the art. Methods of preparing callus from various plants are well known in the art and specific methods are detailed in patents and references used by those skilled in the art. Cultures can be initiated from most of the above-identified tissue. The only true requirement of the transforming material is that it can form a transformed plant. The transgenic genetic material can come from various non-plant genes (such as; bacteria, yeast, animals, and viruses) along with being from plants.

The DNA used for transformation of these plants clearly may be circular, linear, and double or single stranded. Usually, the DNA is in the form of a plasmid. The plasmid usually contains regulatory and/or targeting sequences which assists the expression of the genetic material (transgene) in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

The regulatory promoters employed can be constitutive such as CaMv35S (usually for dicots) and polyubiquitin for monocots or tissue specific promoters such as CAB promoters, etc. The prior art includes but is not limited to octopine synthase, nopaline synthase, CaMv19S, mannopine synthase promoters. These regulatory sequences can be combined with introns, terminators, enhancers, leader sequences and the like in the material used for transformation.

The isolated DNA is then transformed into the plant. The direct transformation of ovum, pollen, and seedlings meristem greatly reduce the difficulties associated with cell regeneration of different plants or genotypes within a plant can present. Duncan, from at least 1985-1988 produced literature on plant regeneration from callus. Both inbred and hybrid callus have resulted in regenerated plants. Somatic embryogenesis has been performed on various maize tissues, which was once considered unusable for this purpose. The prior art clearly teaches the regeneration of plants from various maize tissues.

The most common method of transformation is referred to as gunning or microprojectile bombardment. This biolistic process has small gold-coated particles coated with DNA shot into the transformable material. Techniques for gunning DNA into cells, tissue, callus, embryos, and the like are well known in the prior art.

After the transformation of the plant material is complete, the next step is identifying the cells or material, which has been transformed. In some cases, a screenable marker is employed such as the beta-glucuronidase gene of the uidA locus of *E. coli.* Then, the transformed cells expressing the colored protein are selected for either regeneration or further use. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly effected by the toxic agent by having slower growth rates. If the transformed material was cell lines then these lines are regenerated into plants. The cells' lines are treated to induce tissue differentiation. Methods of regeneration of cellular maize material are well known in the art since early 1982. European Patent Application, publication 160,390, describes tissue culture of corn, which can be used by those skilled in the art. The plants from the transformation process or the plants resulting from a cross using a transformed line or the progeny of such plants are transgenic plants.

Various techniques known to those skilled in the art, such as haploid, transformation, and a host of other conventional and unconventional methods are within the scope of the invention. All plants and plant cells produced using inbred corn line G4901 are within the scope of this invention. The invention encompasses the inbred corn line used in selfing and in crosses with other, different, corn inbreds to produce (F1) corn hybrid seeds and hybrid plants. This invention includes cells, which upon growth and differentiation produce corn plants having the physiological and morphological characteristics of the inbred line G4901.

A deposit of at least 2500 seeds of this invention will be maintained by Garst Seed Company, 2369 330th Street, Slater, Iowa 50244. Access to this deposit will be available during the pendency of this application to the Commissioner of Patents and Trademarks and persons determined by the Commissioner to be entitled thereto upon request. All restrictions on availability to the public of such material will be removed upon issuance of a granted patent of this application by depositing at least 2500 seeds of this invention at the American Type Culture Collection, 10801 University Boulevard, Manassas, Va. 20110. The deposit of at least 2500 seeds will be from the same inbred seed taken from the deposit maintained by Garst Seed Company. The date of the deposit was Jul. 26, 2004 and the seeds were tested and found to be viable on Aug. 3, 2004. The ATCC accession number is PTA-6130. The ATCC deposit will be maintained in that depository, which is a public depository, for a period of 30 years, or 5 years after the last request, or for the enforceable life of the patent, whichever is longer, and will be replaced if it becomes nonviable during that period.

Additional public information on some ZS designations may be available from the PVP office a division of the U.S. government.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

I claim:

1. A method for producing a transformed corn plant, comprising introducing a transgene into a corn plant designated inbred G4901 of which a representative sample of seed of the G4901 plant has been deposited in the ATCC accession number PTA-6130.

2. Hybrid seed produced by the method comprising the following steps:
   (a) planting, seeds of corn inbred G4901 a representative sample of said seed having been deposited in the ATCC accession number PTA-6130 and another inbred line, one of said inbred lines not releasing pollen;
   (b) Cultivating corn plants resulting from said planting;
   (c) Allowing cross pollination to occur between said inbred lines; and
   (d) Harvesting seeds produced on the non-pollen releasing inbred.

3. A first generation (F1) hybrid corn plant produced by using inbred corn plant G4901, a representative sample of seed of the G4901 plant having been deposited in the ATCC accession number PTA-6130, in the process of:
   (a) planting seeds of corn inbred G4901 and another inbred line;
   (b) cultivating corn plants resulting from said planting;
   (c) preventing pollen production by the plants of one of the inbred lines;
   (d) allowing cross-pollination to occur between said inbred lines;
   (e) harvesting seeds produced on plants of the inbred line of step (c); and
   (f) growing a harvested seed of step (e).

4. A transgenic corn plant produced by the method of claim 1.

5. A transgenic seed harvested from the plant according to claim 4.

6. Hybrid seed produced by hybrid combination of plants according to claim 4 and plants of another inbred corn line, wherein the hybrid seed comprises said transgene.

7. An inbred corn plant designated G4901, a representative sample of the seed of G4901 having been deposited in the ATCC accession number PTA-6130, further comprising an additional trait, wherein said trait is introduced by crossing plant G4901 with another corn plant comprising said trait, followed by backcrosses with plant G4901.

8. A seed harvested from the plant according to claim 7, said seed comprising said trait.

9. Hybrid seed produced by hybrid combination of plants of claim 7 and plants of another inbred corn line, wherein the hybrid seed comprises said trait.

10. A method for producing an F1 hybrid corn seed, comprising crossing a plant grown from seeds of corn inbred G4901, a representative sample of said seed having been deposited in the ATCC accession number PTA-6130, with a different corn plant and harvesting the resultant F1 hybrid corn seed.

11. The transgenic corn implant of claim 4, wherein said transgene confers resistance to an herbicide.

12. The corn plant of claim 11, wherein the transgene is selected from the group consisting of: the imazethapyr tolerant gene, the Pat gene, the Bar gene, the EPSP gene.

13. The transgenic corn plant of claim 4, wherein said transgene confers insect resistance.

14. The corn plant of claim 13, wherein the transgene encodes a *Bacillus thuringiensis* Cry gene.

15. The transgenic corn plant of claim 4, wherein said transgene confers disease resistance.

16. Seed produced by a method comprising a) selfing a plant produced by growing a seed of inbred corn line G4901, a representative sample of seed of line G4901 having been deposited in ATCC accession number PTA-6130, or b) crossing two G4901 plants.

* * * * *